United States Patent
Zhang et al.

(10) Patent No.: US 9,662,073 B2
(45) Date of Patent: May 30, 2017

(54) HEART FAILURE EVENT DETECTION USING MULTI-LEVEL CATEGORICAL FUSION

(71) Applicant: Cardiac Pacemakers, Inc., St. Paul, MN (US)

(72) Inventors: Yi Zhang, Plymouth, MN (US); Pramodsingh Hirasingh Thakur, Woodbury, MN (US); Qi An, Blaine, MN (US); Julie A. Thompson, Circle Pines, MN (US); Ramesh Wariar, Blaine, MN (US); Robert J. Sweeney, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/637,447

(22) Filed: Mar. 4, 2015

(65) Prior Publication Data
US 2015/0250428 A1   Sep. 10, 2015

Related U.S. Application Data

(60) Provisional application No. 61/949,313, filed on Mar. 7, 2014.

(51) Int. Cl.
 *A61B 5/00* (2006.01)
 *A61B 5/0205* (2006.01)
 *G06F 19/00* (2011.01)

(52) U.S. Cl.
 CPC .......... *A61B 5/7275* (2013.01); *A61B 5/0205* (2013.01); *A61B 5/4842* (2013.01); *G06F 19/345* (2013.01); *G06F 19/3431* (2013.01)

(58) Field of Classification Search
 CPC ......... A61B 5/0205; A61B 5/021; A61B 5/08; A61B 5/4842; A61B 5/7275; A61B 5/7282; G06F 19/3431; G06F 19/345
 (Continued)

(56) References Cited

U.S. PATENT DOCUMENTS 5,855,593 A * 1/1999 Olson ................ A61B 5/042
                                                       607/4
7,174,203 B2   2/2007 Arand et al.
 (Continued)

FOREIGN PATENT DOCUMENTS

WO   WO-2006125097 A2   11/2006
WO   WO-2010/042790 A2   4/2010
 (Continued)

OTHER PUBLICATIONS

"International Application Serial No. PCT/US2015/018565, International Search Report on Patentability mailed on Sep. 22, 2016", 10 pgs.
 (Continued)

*Primary Examiner* — Christopher A Flory
(74) *Attorney, Agent, or Firm* — Schwegman Lundberg & Woessner, P.A.

(57) ABSTRACT

Systems and methods for detecting a present, or predicting a future, target physiologic event such as worsening heart failure (HF) are described. A system can comprise a patient information receiver circuit, at least two categorical risk analyzer circuits, and a categorical fusion circuit. The patient information receiver circuit receives physiologic signals and generates signal trends. The categorical risk analyzer circuit receives a category-specific input selected from the signal trends according to an associative physiologic condition indicative or correlative of the target event. The categorical risk analyzer circuit produces a signal trend metric indicating relative change in signal strength over time. The categorical risk analyzer circuit calculates a categorical risk index that indicates likelihood of the patient developing or presenting the associative physiologic condition. The categorical fusion circuit uses the categorical risk indices to generate a composite risk indicator indicating
 (Continued)

likelihood of the patient developing the target physiologic event.

20 Claims, 5 Drawing Sheets

(58) Field of Classification Search
USPC .............. 600/301, 481, 483, 508, 509, 529
See application file for complete search history.

(56) References Cited

U.S. PATENT DOCUMENTS

| | | | |
|---|---|---|---|
| 7,480,528 B2 | 1/2009 | Brockway et al. | |
| 2003/0212579 A1* | 11/2003 | Brown | A61B 5/411 705/2 |
| 2006/0282000 A1* | 12/2006 | Zhang | A61B 5/0031 600/528 |
| 2007/0179361 A1* | 8/2007 | Brown | A61B 5/411 600/300 |
| 2007/0259377 A1* | 11/2007 | Urdea | G01N 33/48714 435/7.1 |
| 2008/0009684 A1* | 1/2008 | Corsetti | A61B 5/00 600/300 |
| 2008/0157980 A1 | 7/2008 | Sachanandani et al. | |
| 2009/0076344 A1 | 3/2009 | Libbus et al. | |
| 2010/0073170 A1 | 3/2010 | Siejko et al. | |
| 2010/0081941 A1* | 4/2010 | Naghavi | A61B 5/015 600/481 |
| 2010/0094102 A1 | 4/2010 | Zhang et al. | |
| 2010/0267052 A1* | 10/2010 | Gelber | C12Q 1/6883 435/7.1 |
| 2011/0003707 A1* | 1/2011 | Goix | G01N 33/6893 506/9 |
| 2011/0301982 A1 | 12/2011 | Green, Jr. et al. | |
| 2011/0306845 A1 | 12/2011 | Osorio | |
| 2012/0003639 A1* | 1/2012 | Kerlikowske | G01N 33/57415 435/6.11 |
| 2012/0065514 A1* | 3/2012 | Naghavi | G06F 19/345 600/454 |
| 2012/0157864 A1* | 6/2012 | Thakur | A61B 5/0538 600/508 |
| 2012/0157874 A1* | 6/2012 | Thakur | A61B 5/0205 600/547 |
| 2013/0018234 A1* | 1/2013 | Thompson | A61B 5/0031 600/301 |
| 2013/0095459 A1* | 4/2013 | Tran | A61B 5/6816 434/247 |
| 2013/0116578 A1 | 5/2013 | An et al. | |
| 2013/0261009 A1* | 10/2013 | Goix | G01N 33/6893 506/9 |
| 2013/0345524 A1* | 12/2013 | Meyer | G06F 19/363 600/301 |
| 2014/0031643 A1* | 1/2014 | An | A61B 5/0205 600/309 |
| 2014/0120559 A1* | 5/2014 | Schaefer | G01N 33/6893 435/7.92 |
| 2014/0274891 A1* | 9/2014 | Caffrey | G01N 33/566 514/6.9 |
| 2014/0343439 A1* | 11/2014 | Sweeney | A61B 5/0205 600/484 |
| 2015/0088026 A1* | 3/2015 | Averina | A61B 5/0538 600/547 |
| 2015/0105835 A1* | 4/2015 | Thakur | A61N 1/3627 607/18 |
| 2015/0126878 A1* | 5/2015 | An | A61B 5/01 600/484 |
| 2015/0126883 A1* | 5/2015 | An | A61B 5/02028 600/513 |
| 2015/0157221 A1* | 6/2015 | An | A61B 5/02055 600/301 |
| 2015/0157273 A1* | 6/2015 | An | A61N 1/36585 600/301 |
| 2015/0250428 A1* | 9/2015 | Zhang | A61B 5/4842 600/301 |
| 2015/0265174 A1* | 9/2015 | Shakibi Gilani | A61B 5/0456 600/516 |
| 2015/0265175 A1* | 9/2015 | Shakibi Gilani | A61B 5/0456 600/516 |
| 2015/0327776 A1* | 11/2015 | Zhang | A61B 7/04 600/301 |
| 2015/0342466 A1* | 12/2015 | Thakur | A61B 5/024 600/484 |
| 2015/0342487 A1* | 12/2015 | Thakur | A61B 5/08 600/484 |
| 2015/0342540 A1* | 12/2015 | An | A61B 5/6869 600/484 |
| 2015/0351660 A1* | 12/2015 | An | A61B 5/0535 600/484 |
| 2016/0038093 A1* | 2/2016 | Sharma | A61B 5/7435 600/481 |
| 2016/0091497 A1* | 3/2016 | Goix | G01N 33/6893 506/9 |

FOREIGN PATENT DOCUMENTS

| | | |
|---|---|---|
| WO | WO-2012059477 A1 | 5/2012 |
| WO | WO-2014189885 A1 | 11/2014 |
| WO | WO-2015065674 A1 | 5/2015 |
| WO | WO-2015134556 A1 | 9/2015 |

OTHER PUBLICATIONS

"International Application Serial No. PCT/US2015/018565, Interntional Search Report mailed Jun. 5, 2015", 4 pgs.
"International Application Serial No. PCT/US2015/018565, Written Opinion mailed Jun. 5, 2015", 8 pgs.
"International Application Serial No. PCT/US2015/027947 International Search Report mailed Jul. 1, 2015", 4 pgs.
"International Application Serial No. PCT/US2015/027947 Written Opinion mailed Jul. 1, 2015", 6 pgs.

* cited by examiner

HEART FAILURE EVENT DETECTION USING MULTI-LEVEL CATEGORICAL FUSION

CLAIM OF PRIORITY

This application claims the benefit of priority under 35 U.S.C. §119(e) of U.S. Provisional Patent Application Ser. No. 61/949,313, filed on Mar. 7, 2014, which is herein incorporated by reference in its entirety.

TECHNICAL FIELD

This document relates generally to medical devices, and more particularly, to systems, devices and methods for detecting and monitoring worsening of heart failure.

BACKGROUND

Congestive heart failure (CHF) is a major health problem and affects over five million people in the United States alone. CHF is the loss of pumping power of the heart, resulting in the inability to deliver enough blood to meet the demands of peripheral tissues. CHF patients typically have enlarged heart with weakened cardiac muscles, resulting in reduced contractility and poor cardiac output of blood.

CHF is usually a chronic condition, but can occur suddenly. It can affect the left heart, right heart or both sides of the heart. If CHF affects the left ventricle, signals that control the left ventricular contraction can be delayed, and the left and right ventricles do not contract simultaneously. Non-simultaneous contractions of the left and right ventricles further decrease the pumping efficiency of the heart. Early attention to signs and symptoms of HF decompensation is critical for patient health.

Overview

Frequent monitoring of CHF patients and timely detection of events indicative of heart failure (HF) decompensation status can help prevent worsening HF in CHF patients, hence reducing cost associated with HF hospitalization. Identification of patient at an elevated risk of developing future HF events such as worsening HF can help ensure timely treatment, thereby improving the prognosis and patient outcome. On the other hand, identifying and safely managing patients at tow risk of future HF events can avoid unnecessary medical intervention and reduce healthcare cost.

Ambulatory medical devices can be used for monitoring HF patient and detecting HF decompensation events. Examples of such ambulatory medical devices can include implantable medical devices (IMD), subcutaneous medical devices, wearable medical devices or other external medical devices. Ambulatory or implantable medical devices can include physiologic sensors that can be configured to sense electrical activity and mechanical function of the heart, including variables associated with signs or symptoms associated with either a new or worsening of an existing disease, such as pulmonary edema, pleural effusion, asthma, pneumonia, myocardial infarction, dilated cardiomyopathy, ischemic cardiomyopathy, systolic HF, diastolic HF, valvular disease, renal disease, chronic obstructive pulmonary disease, peripheral vascular disease, cerebrovascular disease, hepatic disease, diabetes, anemia, depression, pulmonary hypertension, sleep disordered breathing, or hyperlipidemia, among others.

The medical device can optionally deliver therapy such as electrical stimulation pulses to a target area, such as to restore or improve cardiac or neural function. Some of these devices can also provide diagnostic features, such as using transthoracic impedance or other sensor signals. For example, fluid accumulation in the lungs can decrease the transthoracic impedance due to the lower resistivity of the fluid than air in the lungs. Fluid accumulation in the lungs can also irritate the pulmonary system which leads to decrease in tidal volume and increase in respiratory rate. In another example, heart sounds can be useful indicators of proper or improper functioning of a patient's heart. Heart sounds are associated with mechanical vibrations from activity of a patient's heart and the flow of blood through the heart. Heart sounds recur with each cardiac cycle, and according to the activity associated with the vibration, heart sounds can be separated and classified into various components including S1, S2, S3, and S4 heart sounds.

Because worsening HV can be a complex process resulting in multifactorial physiologic changes, a single physiologic sensor may not always provide the desired performance for timely and accurate detection or prediction of worsening HF. Some ambulatory medical devices can include multiple physiologic sensors working cooperatively to detect or predict the worsening HF. For example, an ambulatory medical device can include a fusion center that combines the responses of multiple physiologic sensors to create a decision about the worsening HF.

Although sensor fusion may to some extent overcome the limitation of a single physiologic sensor in detecting or predicting worsening HF, challenges remain. For example, a sensor fusion algorithm, or a classifier, is usually designed such that it can detect a type of change in the signatures of the physiologic sensors that are correlative of a particular physiologic manifestation or symptom of worsening HF. However, worsening HF status may not consistently be associated with such changes in the sensor signatures; rather, there can be a wide variety of signs, symptoms, and pathophysiologic manifestations across HF patients, such as dyspnea, pulmonary and/or peripheral edema, dilated cardiomyopathy, ventricular dilation, accentuated S3 heart sound, among others. Even within a patient, the manifestation can vary significantly from one HF decompensation event to another. For example, worsening HF may be manifested as a peripheral congestion or a central congestion, a wet-versus-dry hemodynamic profile or a cold-versus-warm profile. The worsening HF can also co-exist with various comorbidities such as atrial arrhythmia, COPD, pneumonia, hypertension, diabetes and renal dysfunction. Because of high degree of intra-patient and inter-patient variation in symptoms and clinical manifestations of worsening HF, a fusion algorithm that is not specifically designed to address the these variations, may not be robust enough to detect the progression of the HF in a wide range of patients event though it employs multiple physiologic sensors.

Additionally, physiologic sensors used for predicting or detecting worsening HF may be better at detecting one type of pathophysiologic manifestation indicative or correlative of worsening HF than other types of manifestations. For example, a heart sound sensor may be more sensitive and specific to elevated ventricular filling pressure, while other sensors such as a thoracic impedance-based respiration sensor can be more sensitive and specific to dyspnea or tachypnea. Conventional sensor fusion algorithms such as neural networks or decision trees that blend multiple physiologic sensor signals that have different strengths and weakness therefore may not be optimal HF event detection or prediction.

Furthermore, it is clinically desirable that a sensor fusion architecture be capable of providing clinicians with readily interpretable and actionable "intermediate" results such as severity or likelihood of an HF-related signs and symptoms, comorbidity conditions or etiologic factors, or other associative physiologic conditions related to the target event of worsening HF. Yet such information and functionality is not readily available under the conventional sensor fusion algorithms such as neural networks.

Therefore, the present inventors have recognized that there remains a considerable need of systems and methods that can detect target physiologic events indicative of worsening HF or identify CHF patients with elevated risk of developing future events of worsening HF with improved accuracy and reliability, particularly in an ambulatory setting. The present inventors have further recognized that by categorizing physiologic sensors or physiologic signals sensed from those sensors into different groups each dedicated for detecting a specified associative physiologic condition related to worsening HF, a multi-level fusion scheme that pools the outputs from those groups can be used to increase reliability and robustness of detecting or predicting an event such as worsening HF. Moreover, because the fusion is based on outputs that represent various associative physiologic conditions, the fusion scheme is more user-friendly such that it allows the clinicians to readily interpret patient status and take immediate actions such as clinical intervention.

Various embodiments described herein can help improve detection of a target physiologic event or identification of patients at elevated risk of developing a target physiologic event. A system embodiment can comprise a patient information receiver circuit, at least two categorical risk analyzer circuits, and a categorical fusion circuit. The patient information receiver circuit can receive patient information including one or more physiologic signals obtained from a patient and generate a plurality of signal trends from the physiologic signals. Each categorical risk analyzer circuit can receive a category-specific input which includes a portion selected from the plurality of signal trends based on a specified associative physiologic condition indicative or correlative of a target physiologic event. A categorical risk index, which indicates likelihood of the patient developing or presenting the associative physiologic condition, can be calculated using the selected portion of the plurality of signal trends. The categorical fusion circuit can use the categorical risk indices to generate a composite risk indicator that indicates likelihood of the patient developing the target physiologic event.

A system embodiment for detecting or predicting worsening HF can comprise a patient information receiver that receives patient information including one or more physiologic signals, and at least two categorical risk analyzer circuits. The categorical risk analyzer circuit can receive a category-specific input including a portion selected from the signal trends based on an associative physiologic condition. The associative physiologic condition can be indicative or correlative of worsening HF. The categorical risk analyzer circuit can analyze the category-specific input, and produce a signal trend metric including a signal change indicator that indicates a level of signal change, and classify the signal trend metric into one of a plurality of levels indicating relative change in signal strength over time. The signal trend metric can also include a signal strength indicator indicating an amplitude or power of the signal trend, or a signal variability indicator indicating a degree of variation of the signal trend over a specified period of time. The categorical risk analyzer circuit, using the classified levels of the selected signal trends, can further calculate a categorical risk index that indicates likelihood of the patient developing or presenting the associative physiologic condition. The system comprises a categorical fusion circuit that use a linear or nonlinear combination of the categorical risk indices to generate a composite risk indicator indicative of likelihood of the patient developing the worsening HF.

A method embodiment can comprise operations of receiving patient information including one or more physiologic signals obtained from a patient, and generating a plurality of signal trends from the physiologic signals. The method can include receiving at least first and second category-specific inputs. The first category-specific input includes a first portion of signal trends based on a first associative physiologic condition, and a second category-specific input includes a second portion of the signal trends based on a different second associative physiologic condition. The first and second associative physiologic conditions can be indicative or correlative of a target physiologic event. The method can include generating first signal trend metrics for the first portion of the signal trends and second signal trend metrics for the second portion of the signal trends. The signal trend metrics can include at least one of a signal change indicator indicative of a level of signal change, a signal strength indicator indicating an amplitude or power of the signal trend, or a signal variability indicator indicating a degree of variation of the signal trend over a specified period of time. Using the first and second signal trend metrics, respective first and second categorical risk indices can be calculated. The first and second categorical risk indices indicate likelihood of the patient developing or presenting respective first and second associative physiologic conditions. The method also comprise an operation of using the first and second categorical risk indices to compute a composite risk indicator (CRI) that indicates likelihood of a patient developing the target physiologic event.

This Overview is an overview of some of the teachings of the present application and not intended to be an exclusive or exhaustive treatment of the present subject matter. Further details about the present subject matter are found in the detailed description and appended claims, Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for detecting an target physiologic event such as worsening HF, or for identifying patients with elevated risk of developing such an event in the future. The HF event detection or risk stratification can be performed using the physiologic signals sensed from sensors associated with an ambulatory medical device such as an implantable cardiac device. The physiologic signals can be selectively used by at least two categorical risk analyzers each configured to calculate a categorical risk index indicating a likelihood of the patient developing a particular associative physiologic condition indicative or correlative of the target physiologic event. A categorical fusion can then be used to combine the categorical risk indices to produce a detection decision of the target physiologic event, or to predict the risk of future target physiologic event, thereby alerting clinicians to take immediate medical attention to the patient.

Figure 1:
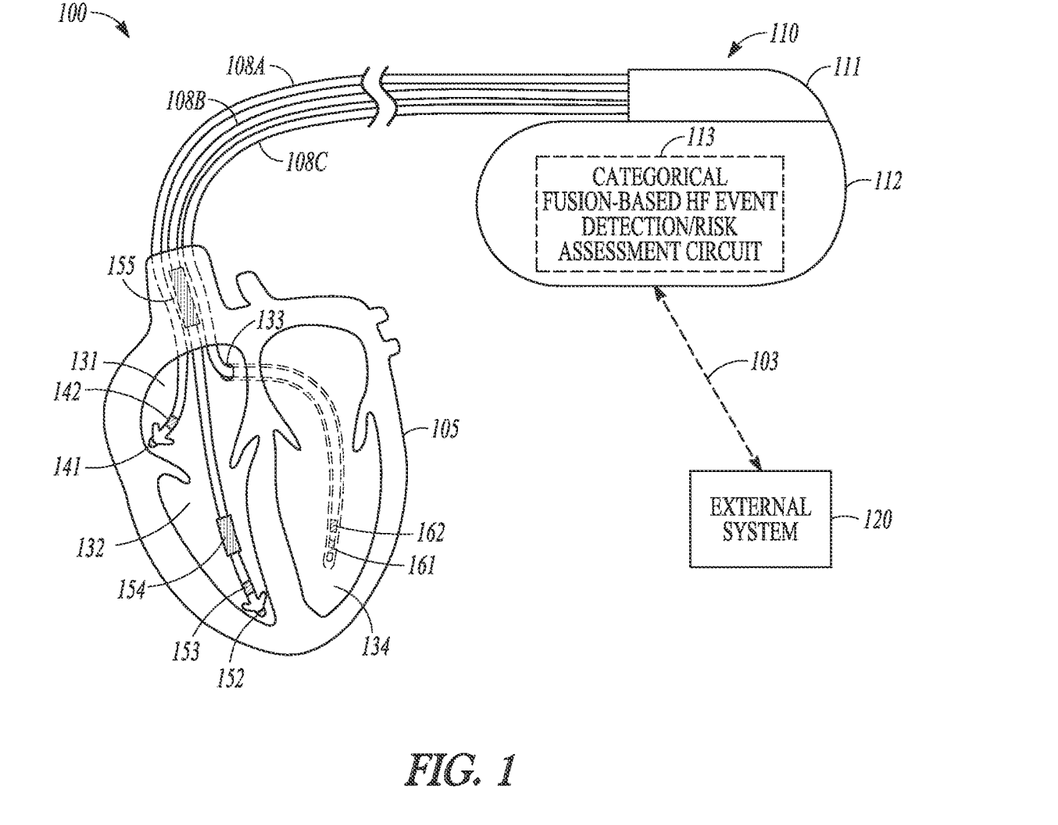
FIG. 1 illustrates an example of a cardiac rhythm management (CRM) system and portions of the environment in which the CRM system operates.

FIG. 1 illustrates an example of a Cardiac Rhythm Management (CRM) system 100 and portions of an environment in which the CRM system 100 can operate. The CRM system 100 can include an ambulatory medical device, such as an implantable medical device (IMD) 110 that can be electrically coupled to a heart 105 such as through one or more leads 108A-C, and an external system 120 that can communicate with the IMD 110 such as via a communication link 103. The IMD 110 may include an implantable cardiac device such as a pacemaker, an implantable cardioverter-defibrillator (ICD), or a cardiac resynchronization therapy defibrillator (CRT-D). The IMD 110 can include one or more monitoring or therapeutic devices such as a subcutaneously implanted device, a wearable external device, a neural stimulator, a drug delivery device, a biological therapy device, a diagnostic only device, or one or more other ambulatory medical devices. The IMD 110 may be coupled to, or may be substituted by a monitoring medical device such as a bedside or other external monitor.

As illustrated in FIG. 1, the IMD 110 can include a hermetically sealed can 112 that can house an electronic circuit that can sense a physiologic signal in the heart 105 and can deliver one or more therapeutic electrical pulses to a target region, such as in the heart, such as through one or more leads 108A-C. The CRM system 100 can include only one lead such as 108B, or can include two leads such as 108A and 108B.

The lead 108A can include a proximal end that can be configured to be connected to IMD 110 and a distal end that can be configured to be placed at a target location such as in the right atrium (RA) 131 of the heart 105. The lead 108A can have a first pacing-sensing electrode 141 that can be located at or near its distal end, and a second pacing-sensing electrode 142 that can be located at or near the electrode 141. The electrodes 141 and 142 can be electrically connected to the IMD 110 such as via separate conductors in the lead 108A, such as to allow for sensing of the right atrial activity and optional delivery of atrial pacing pulses. The lead 108B can be a defibrillation lead that can include a proximal end that can be connected to IMD 110 and a distal end that can be placed at a target location such as in the right ventricle (RV) 132 of heart 105. The lead 108B can have a first pacing-sensing electrode 152 that can be located at distal end, a second pacing-sensing electrode 153 that can be located near the electrode 152, a first defibrillation coil electrode 154 that can be located near the electrode 153, and a second defibrillation coil electrode 155 that can be located at a distance from the distal end such as for superior vena cava (SVC) placement. The electrodes 152 through 155 can be electrically connected to the IMD 110 such as via separate conductors in the lead 108B. The electrodes 152 and 153 can allow for sensing of a ventricular electrogram and can optionally allow delivery of one or more ventricular pacing pulses, and electrodes 154 and 155 can allow for delivery of one or more ventricular cardioversion/defibrillation pulses. In an example, the lead 108B can include only three electrodes 152, 154 and 155. The electrodes 152 and 154 can be used for sensing or delivery of one or more ventricular pacing pulses, and the electrodes 154 and 155 can be used for delivery of one or more ventricular cardioversion or defibrillation pulses. The lead 108C can include a proximal end that can be connected to the IMD 110 and a distal end that can be configured to be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C can include an electrode 161 that can be located at a distal end of the lead 108C and another electrode 162 that can be located near the electrode 161. The lead 108C can include one or more electrodes in addition to the electrodes 161 and 162 along the body of the lead 108C. The electrodes 161 and 162, and any additional electrodes on the lead 108C, can be electrically connected to the IMD 110 such as via separate conductors in the lead 108C such as to allow for sensing of the LV electrogram and optionally allow delivery of one or more resynchronization pacing pulses from the LV.

The IMD 110 can include an electronic circuit that can sense a physiologic signal. The physiologic signal can include an electrogram or a signal representing mechanical function of the heart 105. The hermetically sealed can 112 may function as an electrode such as for sensing or pulse delivery. For example, an electrode from one or more of the leads 108A-C may be used together with the can 112 such as for unipolar sensing of an electrogram or for delivering one or more pacing pulses. A defibrillation electrode from the lead 108B may be used together with the can 112 such as for delivering one or more cardioversion/defibrillation pulses. In an example, the IMD 110 can sense impedance such as between electrodes located on one or more of the leads 108A-C or the can 112. The IMD 110 can be configured to inject current between a pair of electrodes, sense the resultant voltage between the same or different pair of electrodes, and determine impedance using Ohm's Law. The impedance can be sensed in a bipolar configuration in which the same pair of electrodes can be used for injecting current and sensing voltage, a tripolar configuration in which the pair of electrodes for current injection and the pair of electrodes for voltage sensing can share a common electrode, or tetrapolar configuration in which the electrodes used for current injection can be distinct from the electrodes used for voltage sensing. In an example, the IMD 110 can be configured to inject current between an electrode on the RV lead 108B and the can housing 112, and to sense the resultant voltage between the same electrodes or between a different electrode on the RV lead 108B and the can housing 112. A physiologic signal can be sensed from one or more physiologic sensors that can be integrated within the IMD 110. The IMD 110 can also be configured to sense a physiologic signal from one or more external physiologic sensors or one or more external electrodes that can be coupled to the IMD 110. Examples of the physiologic signal can include one or more of heart rate, heart rate variability, arrhythmia information, intrathoracic impedance, intracardiac impedance, arterial pressure, pulmonary artery pressure, left atrial pressure, RV pressure, LV coronary pressure, coronary blood temperature, blood oxygen saturation, one or more heart sounds, systolic time intervals, heart sound based time intervals, physical activity or exertion level, physiologic response to activity, posture, respiration, body weight, or body temperature.

The arrangement and functions of these leads and electrodes are described above by way of example and not by way of limitation. Depending on the need of the patient and the capability of the implantable device, other arrangements and uses of these leads and electrodes are possible.

As illustrated, the CRM system 100 can include a categorical fusion-based HF event detection/risk assessment circuit 113. The categorical fusion-based HF event detection or risk assessment circuit 113 can receive patient information including one or more physiologic signals obtained from a patient. The physiologic signals can be electrical or mechanical signals that are indicative or correlative of worsening HF. For example, the physiologic signals can include electrograms sensed using ambulatory physiologic sensors deployed on or within the patient and communicated with the IMD 110, such as electrodes on one or more of the leads 108A-C and the can 112. The physiologic signal can also include signals sensed by one or more ambulatory sensors, including blood pressure signals, heart sound signals, bio-impedance signals, respiration signals, posture, activity, heart rate or activity signals, or physiologic response to activity (PRA) signals, among others. The categorical fusion-based HF event detection or risk assessment circuit 113 can include an ensemble of categorical risk analyzers. Each categorical risk analyzers can operate on a selected portion of the physiologic signals or signal features, and calculate a categorical risk index using an intra-category sensor fusion method. The selection of physiologic signals can be based on an associative physiologic event the categorical risk analyzer is purported to detect. The associative physiologic events can include patient clinical signs and manifestations, etiology, comorbidities, therapy history, among others. The categorical fusion-based HF event detection or risk assessment circuit 113 can include a categorical fusion circuit that generates a composite risk indicator (CRI) using an inter-category sensor fusion of some or all of the categorical risk indices. The CRI can be indicative of the likelihood of the patient developing a future event of worsening HF. Examples of the categorical fusion-based HF event detection or risk assessment circuit 113 are described below, such as with reference to FIGS. 2-4.

The external system 120 can allow for programming of the IMD 110 and can receive information about one or more signals acquired by IMD 110, such as can be received via a communication link 103. The external system 120 can include a local external IMD programmer. The external system 120 can include a remote patient management system that can monitor patient status or send commands to the IMD 110 such as to program diagnostic functions or to adjust one or more therapies such as from a remote location.

The communication link 103 can include one or more of an inductive telemetry link, a radio-frequency telemetry link, or a telecommunication link, such as an internet connection. The communication link 103 can provide for data transmission between the IMD 110 and the external system 120. The transmitted data can include, for example, real-time physiologic data acquired by the IMD 110, physiologic data acquired by and stored in the IMD 110, therapy history data or data indicating IMD operational status stored in the IMD 110, one or more programming instructions to the IMD 110 such as to configure the IMD 110 to perform one or more actions that can include physiologic data acquisition such as using programmably specifiable sensing electrodes and configuration, device self-diagnostic test, or delivery of one or more therapies.

The categorical fusion-based HF event detection or risk assessment circuit 113 may be implemented at the external system 120, which can be configured to perform HF risk stratification such as using data extracted from the 110 or data stored in a memory within the external system 120. Portions of the categorical fusion-based HF event detection or risk assessment circuit 113 may be distributed between the IMD 110 and the external system 120.

Portions of the IMD 110 or the external system 120 can be implemented using hardware, software, or any combination of hardware and software. Portions of the IMD 110 or the external system 120 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. For example, a "comparator" can include, among other things, an electronic circuit comparator that can be constructed to perform the specific function of a comparison between two signals or the comparator can be implemented as a portion of a general-purpose circuit that can be driven by a code instructing a portion of the general-purpose circuit to perform a comparison between the two signals. While described with reference to the IMD 110, the CRM system 100 could include a subcutaneous medical device (e.g., subcutaneous ICD, subcutaneous diagnostic device), wearable medical devices (e.g., patch based sensing device), or other external medical devices.

Figure 2:
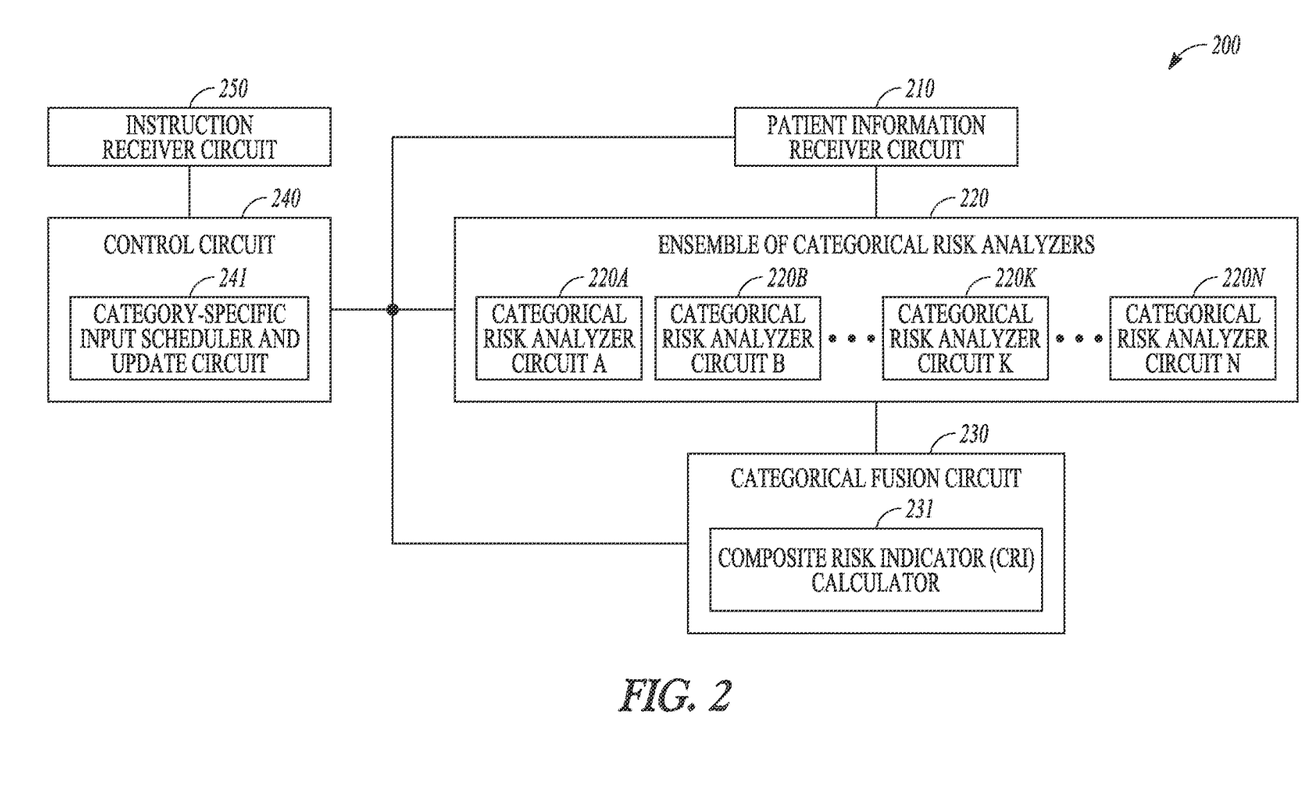
FIG. 2 illustrates an example of a categorical fusion-based HF event prediction system.

FIG. 2 illustrates an example of a categorical fusion-based HF event prediction system 200, which can be an embodiment of the categorical fusion-based HF event detection or risk assessment circuit 113. The categorical fusion-based HF event prediction circuit 200 can be implemented within the IMD 110, or it can be implemented in an external system such as a local or remote patient monitor or patient management system such as the external system 120, which is configured for providing the patient's diagnostic information to an end-user. The categorical fusion-based HF event prediction circuit 200 can include one or more of a patient information receiver circuit 210, an ensemble of categorical risk analyzers 220, a categorical fusion circuit 230, a controller circuit 240, and an instruction receiver circuit 250.

The patient information receiver circuit 210 can be configured to receive patient information including one or more physiologic signals obtained from a patient. The physiologic signals can be sensed using one or more ambulatory physiologic sensors. Examples of such a physiologic signal can include one or more of surface or subcutaneous electrocardiograph (ECG), electrograms such as sensed using electrodes from one or more of the leads 108A-C or the can 112, heart rate, heart rate variability, arrhythmia information, intrathoracic impedance, intracardiac impedance, arterial pressure, pulmonary artery pressure, left atrial pressure, RV pressure, LV coronary pressure, coronary blood temperature, blood oxygen saturation, one or more heart sounds, systolic time intervals, heart sound based time intervals, physiologic response to activity, apnea hypopnea index, one or more respiration signals such as a respiration rate signal, a tidal volume signal, a minute ventilation signal, or rapid shallow breathing index (RR/TV) signal. The physiologic signals can also include one or more of brain natriuretic peptide (BNP), blood panel, sodium and potassium levels, glucose level and other biomarkers and bio-chemical markers. The physiologic signals can also include device therapy statistics such as a percentage of biventricular or left-ventricular only pacing in patient with ambulatory medical devices.

The patient information receiver circuit 210 can generate a plurality of signal trends from the received physiologic signals. The signal trend can be a time series of one or more signal statistical or morphological features calculated from the physiologic signals, indicating relative change in the signal features over time. Examples of signal features can include mean, median, or other central tendency measures; a histogram of the signal intensity; a plurality of signal trends over time; one or more signal morphological descriptors; one or more signal change or rate of change features; one or more signal change or rate of change features, or signal power spectral density at a specified frequency range. The signal features can include components corresponding to physiologic activities. For example, the electrocardiogram or electrogram features can include P wave, R wave, T wave, QRS complex, or other components representing depolarization, hyperpolarization, repolarization, or other electrophysiological properties of the myocardium. The heart sound features can include relative timing (such as with respect to R wave), amplitude, or morphologic characteristics of one or more of S1, S2, S3, or S4 heart sounds. The thoracic impedance features can include maximum, minimum, mean, variance, rate of change, or other statistical or morphological features. The respiration signal features can include respiration rate, respiration depth, tidal volume, minute ventilation, rapid shallow breathing index (RR/TV), or other descriptors.

The patient information receiver circuit 210 can also receive patient health information including, for example, past and present medication and therapy information, or medical history information. The patient information receiver circuit 210 can also receive other non-clinical information such as patient demographic information, or social and behavioral information (e.g., smokers or non-smokers). The physiologic signals and the signal trends derived thereof or other patient health or non-clinical information can be indicative or correlative of the target physiologic event such as progression of HF.

In addition to or as an alternative of acquiring the patient information using physiologic sensors, the patient information receiver circuit 210 can be coupled to the storage device, such as an electronic medical record (EMR) system, and retrieve from the storage device one or more patient historical physiologic signals in response to a command signal. The command signal can be issued by a system user (e.g., a health-care professional) such as via an input device coupled to the instruction receiver 250, or generated automatically by the system in response to a specified event. The patient information receiver circuit 210 can include one or more sub-circuits that can perform signal conditioning or pre-processing, including signal amplification, digitization, or filtering, on the one or more physiologic signals.

The ensemble of categorical risk analyzers 220 can include at least two categorical risk analyzer circuits 220A-220N. Each categorical risk analyzer circuit can be configured to take as a category-specific input a selected portion of the physiologic signals, signal trends, or selected patient health or non-clinical information produced by the patient information receiver circuit 210. The category-specific inputs to the categorical risk analyzer circuits 220A-220N can be non-identical to each other, such that different categorical risk analyzer circuits can detect or predict a distinct associative physiologic condition. In some examples, at least some category-specific inputs of two different categorical risk analyzer circuits can be obtained from physiologic signals sensed from the same physiologic sensor.

The categorical risk analyzer circuits 220A-220N can represent different categories of associative physiologic conditions, and individually estimate the presence or severity of a particular associative physiologic condition. Selection of category-specific input for each of the categorical risk analyzer 220A-220N can be based on a specified associative physiologic condition for that categorical risk analyzer. Various associative physiologic conditions have been identified, including patient clinical signs and manifestations, etiology, comorbidities, therapy history, among others. Examples of the categorical risk analyzer circuits and the selection of category-specific input based on a specified associative physiologic condition are described below, such as with reference to FIGS. 3-4.

Each categorical risk analyzer circuit can calculate a categorical risk index using an intra-category sensor fusion of the category-specific input. The categorical risk index can indicate a likelihood of the patient developing or presenting an associative physiologic event indicative or correlative of a target physiologic event, such as worsening HF. The intra-category fusion can be accomplished by using one or a combination of fusion algorithms including a rule-based model, a decision tree model, a regression model, a neural network model, a random forest, a voting model, a fuzzy logic model, a support vector machine model, or any mathematical model that operates on time-series data. In an example, the categorical risk analyzer circuits 220A-220N can have non-identical fusion mechanisms.

The categorical risk index can be a numerical value such as a probability indicating a likelihood of the patient developing the associative physiologic condition. The categorical risk index can also be a class label indicating presence or absence of the associative physiologic condition, or a label or a number indicating tiered severity of the associative physiologic condition (e.g., High, Medium, or Low; or scores of 1, 2, or 3). Examples of the categorical risk analyzer circuits are described below, such as with reference to FIG. 3.

The categorical fusion circuit 230, coupled to the categorical risk analyzer circuits 220A-220N, can include a composite risk indicator (CRI) calculator 231 configured to calculate a CRI using inter-category fusion of some or all of the categorical risk indices produced by the categorical risk analyzer circuits 220A-220N, The CRI can be indicative of a likelihood of the patient developing a target physiologic event such as worsening HF. In an example, the CRI can be in a form of a classification decision taken from two or more classes indicating various levels of likelihood of having an impending event of worsening HF. For example, if the categorical risk indices are class labels (e.g., High, Medium, or Low severity levels of an associative condition of pulmonary edema), the CRI calculator 231 can compute the CRI using a decision fusion of the class labels produced by the categorical risk analyzer circuits 220A-220N. Examples of the decision fusion method can include majority voting, X-out-of-Y voting, or weighted voting, among others.

The CRI can be a numerical quantity indicating the likelihood of an impending target physiologic event such as worsening HF. For example, if the categorical risk indices are probability values indicating the confidence level of patient developing various types of associative physiologic conditions, the CRI calculator 231 can compute the CRI using a probability fusion of the probability values produced by the categorical risk analyzer circuits 220A-220N. Examples of the probability fusion method can include linear or a non-linear combination such as average or weighted summation, or parametric or non-parametric methods such as a decision tree, a neural networks, a Bayesian network, among other machine learning methods.

The inter-category fusion used in CRI computation can be modified by the system end-user or automatically adjusted. The update can be adapted to changing patient context including patient health condition, activities or behaviors, development of new comorbidities, progression of the target physiologic event, or other patient clinical or non-clinical information. In an example where the CRI is computed as a weighted combination of the categorical risk indices, in patients with renal disease, the CRI calculator 231 can reduce the weight assigned to the categorical risk index computed using thoracic impedance, because with the presence of renal dysfunction, change in thoracic impedance or signal trend derived thereof can be less specific to events of worsening HF. The categorical risk index thus computed may have a degraded performance (e.g., higher false positive rate) in predicting a future event of worsening HF. In another example, in patients with chronic obstructive pulmonary disease (COPD), the weights assigned to the categorical risk index computed using respiration rate or other respiration signals or signal trend can be increased, because with the presence of COPD, change in respiration rate can be more sensitive or specific to events of worsening HF. In yet another example, in patients presenting with a high baseline respiratory rate such as due to renal dysfunction, asthma, or other pulmonary diseases, the CRI calculator 231 can reduce the weight assigned to the categorical risk index computed using respiration rate, while increase the weight assigned to the categorical risk index computed using tidal volume, because the respiration rate in these patients is less sensitive to events of worsening HF.

The modification of the inter-category fusion can also be made in response to a change in performance, reliability, or robustness of a category-specific input (such as a physiologic signal or a signal trend) to the categorical risk analyzer circuits. For example, the categorical risk index that is substantially higher or lower than other categorical risk indices is suspected to be less reliable or potentially affected by interferences or confounding factors, and therefore can be discounted with a reduced weight. In other examples, the inter-category fusion can be modified in response to changing environmental context such as implantable lead revisions, compromise in sensor integrity and quality, or ambient environmental changes. The modification can also be made in response to a change in significance of an associative physiologic condition according to updated domain knowledge such as established evidence of high correlation between an associative physiologic condition and the target physiologic event.

The categorical fusion circuit 230 can generate a report to inform, warn, or alert a system end-user an elevated risk of a patient developing a target physiologic event such as a future worsening HF event. The report can include the CRI with corresponding timeframe within which the risk is predicted. The report can also include recommended actions such as confirmative testing, diagnosis, or therapy options. The report can be presented in one or more media formats including, for example, a textual or graphical message, a sound, an image, or a combination thereof. In an example, the report can be presented to the user via an interactive user interface on the instruction receiver circuit 250. The categorical fusion circuit 230 can also generate and present to the end-user, such as via the external device 120 or the instruction receiver circuit 250, the categorical risk indices computed by the categorical risk analyzer circuits 220A-220N.

The controller circuit 240 can receive external programming input from the instruction receiver circuit 250. The instruction receiver circuit 250 can include a user interface configured to present programming options to the user and receive user's programming input. In an example, at least a portion of the instruction receiver circuit 250, such as the user interface, can be implemented in the external system 120. Using the received programming input, the controller circuit 240 can control the operations of the patient information receiver circuit 210, the ensemble of categorical risk analyzers 220, the categorical fusion circuit 230, and the data flow and instructions between these components.

The control circuit 240 can include a category-specific input scheduler and update circuit 241 which controls selection of category-specific inputs for each of the categorical risk analyzer circuits 220A-220N. The selection can be based on the specified associative physiologic condition of the categorical risk analyzer circuit. Examples of the associative physiologic conditions can include patient clinical signs and manifestations, etiology, comorbidities, therapy history, transitions along the continuum of care such as from home to hospital or vice versa, among others. The selection of the category-specific input can also be based on types or modalities of the physiologic sensors used for measuring the physiologic signals, performance statistics of the physiologic signals or signal trends in detecting a particular associative physiologic condition in a patient population, or a patient-specific historical performance of the physiologic signals or signal trends in detecting the associative physiologic condition.

The category-specific input to the categorical risk analyzer circuits 220A-220N can be non-static; and the category-specific input scheduler and update circuit 241 can adapt the category-specific input selection to changes in a patient context or an environmental context. Examples of the change in patient or environmental contexts can include changes in individual patient's physical and health condition, surgeries, change in sensor placement, implantable lead revisions, compromise in sensor integrity, sensor signal quality, and environmental changes, among others. For example, following a lead revision, performance of a thoracic impedance vector in predicting pulmonary edema may be affected due to the positional change of the electrodes used for measuring the thoracic impedance. The category-specific input scheduler and update circuit 241 can remove an existing sensor signal or information piece (such as the thoracic impedance in the present example) from the category-specific input. Likewise, the category-specific input scheduler and update circuit 241 can add a new sensor signal or information piece to the category-specific input if the new sensors signal or information piece better suited for detecting the associative physiologic condition following the change in patient or environmental contexts.

Removing an existing sensor signal or information piece from the category-specific input, or adding a new one to the category-specific input, can be based on the change in performance of the sensor signal or information piece. In an example, adding or removing a sensor signal or information piece can be based on the relative performance in comparison with other sensor signals or patient health or non-clinical information in the category-specific input. The performance can include accuracy and consistency of a sensor signal or information piece in detecting the associative physiologic condition. For example, in a category-specific input that consists of N sensor signals or information pieces $\{X_1, X_2, \ldots, X_N\}$ designated for detecting an associative physiologic condition of pulmonary edema, if $X_j$ experiences non-significant and least changes than a specified significant number of other sensor signals (such as all of $\{X_1, X_2, \ldots, X_N\}$ except $X_j$, or 2/3 of $\{X_1, X_2, \ldots, X_N\}$), then $X_j$ can be removed from the category-specific input. In some examples, adding or removing a sensor signal or information piece can be based on updated domain knowledge, such as established evidence of high predictive value of a physiologic sensor signal or a patient information piece in predicting or detecting the associative physiologic condition.

As an alternative or in addition to removing or adding a sensor signal or information piece, the category-specific input scheduler and update circuit 241 can reduce the weights to the signal trends or patient health or non-clinical information, if one or more of the categorical risk analyzer circuits 220A-220N uses linear or nonlinear combination of multiple signal trends or patient health or non-clinical information for detecting the associative physiologic conditions.

Figure 3:
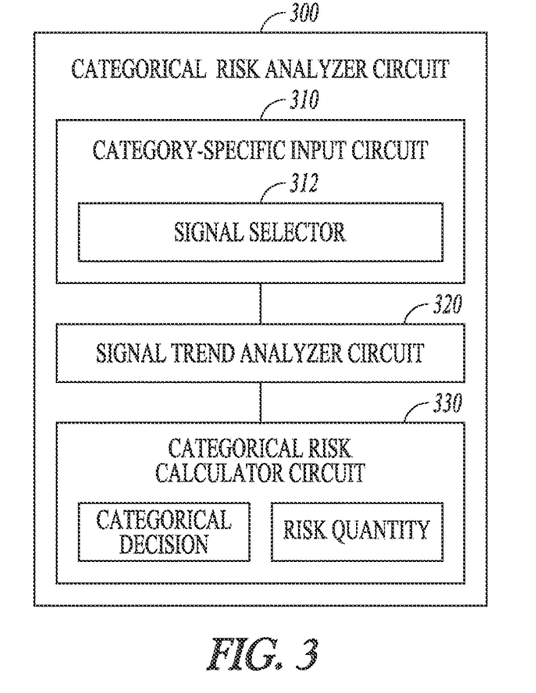
FIG. 3 illustrates an example of a categorical risk analyzer circuit in a categorical fusion-based HF event prediction system.

FIG. 3 illustrates an example of a categorical risk analyzer circuit 300, which can be an embodiment of any one of the categorical risk analyzer circuits 220A-220N. The categorical risk analyzer circuit 300 can be configured to calculate a categorical risk index indicating a likelihood of the patient developing or presenting an associative physiologic condition. The categorical risk analyzer circuit 300 can include one or more of a category-specific input selection circuit 310, a signal trend analyzer circuit 320, and a categorical risk calculator circuit 330.

The category-specific input selection circuits 310 can be coupled to the patient information receiver circuit 210, and configured to receive a category-specific input including a portion of the physiologic signals, signal trends, or patient health or non-clinical information selected from the patient information receiver circuit 210. The category-specific input selection circuits 310 can include a signal selector 312 coupled to and controlled by the category-specific input scheduler and update circuit 241. The signal selector 312 can receive the category-specific input based on the associative physiologic condition. The associative physiologic condition for the categorical risk analyzer circuit 300 can be programmed by an end-user such as via the instruction receiver circuit 250. The associative physiologic condition can also be pre-determined and stored in a memory from which the signal selector 312 can retrieve.

As previously discussed with reference to FIG. 2, the associative physiologic conditions can include patient clinical signs and manifestations, etiology, comorbidities, therapy history, among others. The category-specific input can be adaptively updated according to the changes in patient context or environment context, or changes in performances of a physiologic signal, a signal trend, or a piece of patient health or non-clinical information in a category-specific input. Examples of the signal selector based on the specified associative physiologic condition are discussed below, such as with reference to FIG. 4.

The signal trend analyzer circuit 320 can be configured to generate, for at least one selected portion of the plurality of signal trends, a signal trend metric of signal strength or variation of the signal strength. In an example, the signal trend metric can include a signal change indicator indicative of a level of signal change. When a signal trend is generated as a time series of one or more signal statistical or morphological features derived from physiologic signals, the signal change indicator can be indicative of changes of the strength of the signal trend over time. The signal change indicator can be one of a plurality of pre-determined signal change levels (such as High, Medium, and Low). For example, for a signal trend such as a time series of daily maximum thoracic impedance ($Z_{DailyMax}$) average of $Z_{DailyMax}$ over a first time window and average of $Z_{DailyMax}$ over a second time window can be computed. The first and second time window can non-identical time periods during which $Z_{DailyMax}$ is measured. Difference of the signal strength, such as the difference between the average $Z_{DailyMax}$ computed from the first and second time windows, can be compared to one or more thresholds or value ranges to classify the signal trend into one of the pre-determined levels that represent the signal change indicators. In another example, the signal trend metric can include a signal strength indicator indicating an amplitude or power of the signal trend. The signal strength indicator can be one of a plurality of pre-determined signal strength levels (such as High, Medium, and Low) based on a comparison of the amplitude or power of the signal trend to one or more thresholds. In yet another example, the signal trend metric can include a signal variability indicator indicating a degree of variation over a specified period of time. An example of the signal variability includes measurements of daily variation of respiration rate. The signal variability indicator can be one of a plurality of pre-determined signal variability levels (such as High, Medium, and Low) based on a comparison of the measured signal variability of the signal trend to one or more thresholds.

The categorical risk calculator circuit 330 can be configured to calculate a categorical risk index. In an example, the categorical risk index can be computed as a linear or a nonlinear combination of the signal change indicators of the selected portion of the plurality of signal trends. When the patient information receiver circuit 210 receives patient health or non-clinical information such as demographic information nor therapy information, the categorical risk calculator circuit 330 can calculate the categorical risk index using the patient health or non-clinical information. For example, a score can be assigned to a patient who belongs to a particular demographic group, such as age, gender, or ethnicity. The score can indicate the patient's risk of developing or presenting a particular associative physiologic condition. In an example, the score can be based on the domain knowledge such as established evidence of correlation between the patient health or non-clinical information and the associative physiologic condition. The categorical risk index can be computed as a linear or a nonlinear combination of the signal change indicators of the selected portion of the plurality of signal trends and the scores associated with the patient health or non-clinical information. The categorical risk index can be in a form of class labels indicating a categorical decision, or a numerical quantity representing a probability of the patient later developing an associative physiologic event such as worsening HF.

Figure 4:
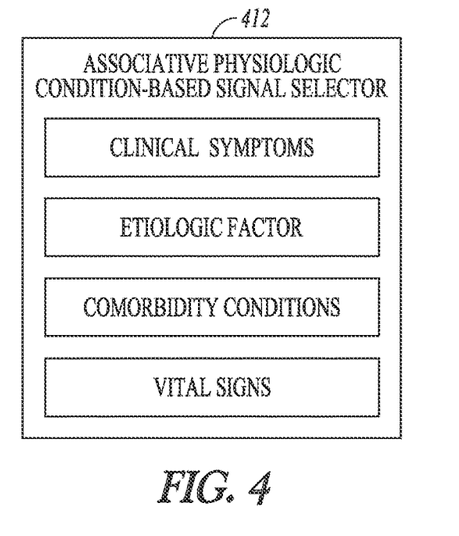
FIG. 4 illustrates an example of a signal selector based on associative physiologic condition.

FIG. 4 illustrates an example of a signal selector 412 based on specified associative physiologic condition. The signal selector 412 can be an embodiment of the signal selector 312. The signal selector 412 can be configured to select a portion from a plurality of physiologic signals, signal trends, or patient health or non-clinical information based on the specified associative physiologic condition. The selected signals or patient information constitute the category-specific input to the categorical risk analyzer circuit (such as 300 or one of 220A-220N), and can be used to calculate a categorical risk index.

The associative physiologic condition can include a variety of clinical manifestations or indicators of patient health status. As illustrated in FIG. 4, the associative physiologic condition can include a specified patient symptom, such as a symptomatic pulmonary event. Examples of the symptomatic pulmonary event can include pulmonary edema, asthma and pneumonia, chronic obstructive pulmonary disease. For example, if a categorical risk analyzer circuit (such as 300 or one of 220A-220N) is designated for detecting a symptomatic pulmonary event, the associative physiologic condition-based signal selector 412 can select physiologic signals or signal trends that are sensitive or specific to the pulmonary event, including one or a combination of daily average transthoracic impedance, tidal volume, respiration rate, or apnea-hypopnea index, among others.

The specified patient symptom can include symptomatic cardiac event. Examples of the symptomatic cardiac event can include atrial or ventricular arrhythmia, myocardial infarction event, coronary artery disease, heart attack event, percentage of pacing or bi-ventricular pacing received by the patient, or amount of pacing relative to amount of sensing of cardiac activations. If a categorical risk analyzer circuit is designated for detecting a symptomatic cardiac event, the associative physiologic condition-based signal selector 412 can select physiologic signals or signal trends that are sensitive or specific to the cardiac event, including one or a combination of intrathoracic impedance, pulmonary arterial pressure, activity level, posture, S1 heart sound strength, S3 heart sound strength, systolic timing interval, or pre-ejection and ejection time, among others.

The associative physiologic condition can also be a specific type of the symptomatic pulmonary event or a symptomatic cardiac event. The associative physiologic condition-based signal selector 412 can select a portion of the physiologic signals or signals trend according to the specific type of the pulmonary event or cardiac event. For example, if a categorical risk analyzer circuit is designated for detecting a pulmonary edema, one or more thoracic impedance signals, and the signal trends derived thereof can be selected. If a categorical risk analyzer circuit is designated for detecting a dyspnea or tachypnea, one or more of respiration rate, rapid shallow breathing index, or tidal volume can be selected. If a categorical risk analyzer circuit is designated for detecting an elevated ventricular filling pressure, one or more of S3 heart sound signals, ventricular pressure signals, pulmonary arterial pressure signal, the statistical or morphological signal features derived thereof can be selected.

The associative physiologic condition can include a specified etiologic factor of the target physiologic event. The etiologic factors can include an underlying disease or a condition that causes the target physiologic event. It may also include disease or conditions that initiates, triggers, exacerbates, or alters the progression of the target physiologic event. For example, in predicting or detecting a target event of worsening HF, the etiologic factors can include one or more of a cardiac arrhythmia, coronary artery disease, heart attack, cardiomyopathy, or structural heart disease, among others. If a categorical risk analyzer circuit is designated for detecting an etiologic factor of ischemic cardiomyopathy, the associative physiologic condition-based signal selector 412 can select one or more of an electrocardiograph (ECG), an intracardiac electrogram, heart sound signal, a chest acceleration signal, and the statistical or morphological features derived thereof (e.g., ST segments measurement or T-wave alternans derived from the ECG signal, or S3 amplitude or other heart sound components derived from heart sound or acceleration signal.)

The etiologic factors of the target physiologic event can be identified based on the domain knowledge, such as based on examination of a patient population developing or presenting the target physiologic event. The etiologic factors can also include a patient-specific risk stratifier that precipitates the target physiologic event. For example, in accordance with the patient-specific risk stratifier, the associative physiologic condition-based signal selector 412 can select signals or signal trends including mean S3 heart sound amplitude, heart sound based pre-ejection period (HS-PEP) signal, heart sound based total ejection time (HS-ET) signal, heart rate signal, variation in respiratory rate signal, or an activity signal.

The associative physiologic condition can include a specified comorbidity condition of a patient. The comorbidity condition is different from, but co-exists with the target physiologic event. For example, comorbidity conditions in worsening HF can be cardiac or non-cardiac, including hypertension, atrial fibrillation, respiratory dysfunctions such as pneumonia or chronic obstructive pulmonary disease (COPD), diabetes mellitus, or renal dysfunction such as renal insufficiency or renal failure, among others. In an example, if the designated associative physiologic condition is renal insufficiency, the associative physiologic condition-based signal selector 412 can select physiologic signals or signal trends including measurements of levels of creatinine or body urea nitrogen (BUN), BUN/creatinine ratio, or glomerular filtration rate (GFR). In another example, in accordance with the comorbidity condition of diabetes mellitus, the physiologic signals or signal trends can include glucose level. In another example, if a categorical risk analyzer circuit is designated for detecting a comorbidy condition of hypertension, the associative physiologic condition-based signal selector 412 can select blood pressure sensor signal such as using an ambulatory pressure sensor.

In some examples, the associative physiologic condition can include specified patient vital signs. The vital signs can indicative of one or more of a cardiac exertion, a pulmonary exertion, a blood pressure, or level of blood oxygenation. For example, in accordance with the cardiac exertion being designated as the associative physiologic condition, the associative physiologic condition-based signal selector 412 can select heart rate signals, signals indicative of cardiac output signal, or S1 heart sound signal, among others.

Figure 5:
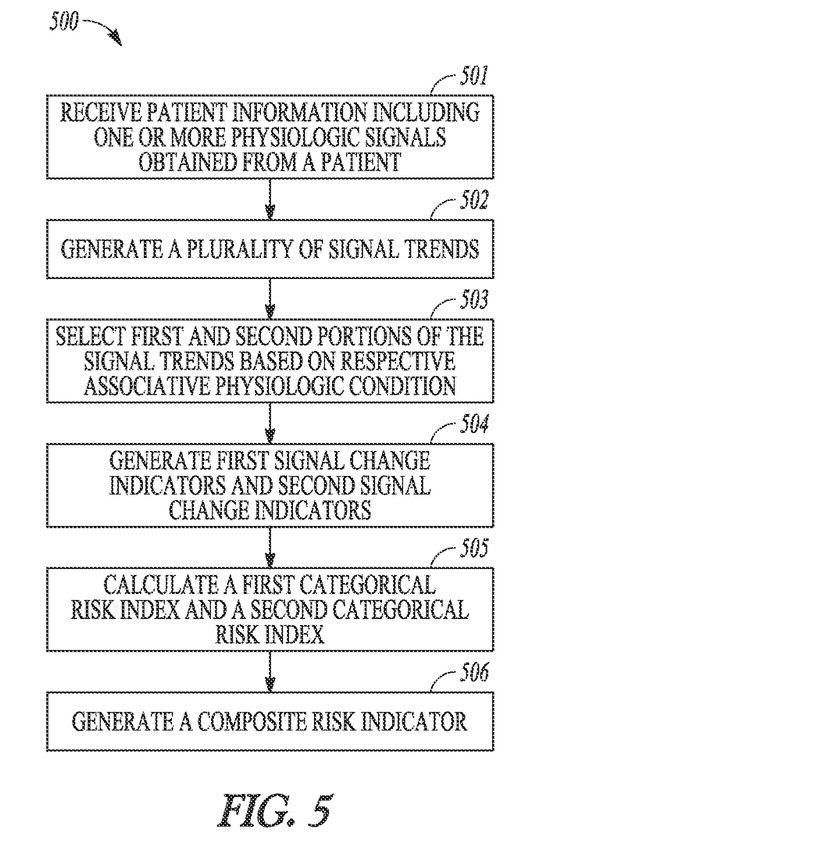
FIG. 5 is a flowchart illustrating an example of a method for predicting a patient's risk of developing an event indicative of worsening HF.

FIG. 5 is a flowchart illustrating an example of a method 500 for predicting a patient's risk of developing a target physiologic event such as worsening HF. The method 500 can be implemented and operate in an ambulatory medical device or in a remote patient management system. In an example, the method 500 can be performed by the categorical fusion-based HF event detection or risk assessment circuit 113 implemented in the IMD 110, or in the external device 120 which can be in communication with the IMD 110. In addition to predicting worsening HF, the method 500 can be modified for use in identifying patients at elevated risk of developing a new or worsening of an existing disease, such as pulmonary edema, pulmonary condition exacerbation, asthma and pneumonia, myocardial infarction, dilated cardiomyopathy, ischemic cardiomyopathy, systolic diastolic HF, valvular disease, renal disease, chronic obstructive pulmonary disease, peripheral vascular disease, cerebrovascular disease, hepatic disease, diabetes, asthma, anemia, depression, pulmonary hypertension, sleep disordered breathing, or hyperlipidemia, among others.

At 501, patient information, including one or more physiologic signals obtained from a patient, can be received. The physiologic signals can be sensed using one or more physiologic sensors associated with the patient. Examples of such a physiologic signal can include one or more electrograms sensed from the electrodes on one or more of the leads 108A-C or the can 112, electrocardiogram, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, systolic time intervals, heart sound based time intervals, physiologic response to activity, apnea hypopnea index, one or more respiration signals such as a respiration rate signal, a tidal volume signal, a minute ventilation signal, or a rapid shallow breathing index (RR/TV) signal. The physiologic signals can also include one or more of brain natriuretic peptide (BNP), blood panel, sodium and potassium levels and glucose level. The physiologic signals can also include device therapy statistics such as a percentage of biventricular or left-ventricular only pacing in patient with ambulatory medical devices. The physiologic signals can be acquired from a patient and stored in a storage device such as an electronic medical record (EMR) system. The physiologic signals can be preprocessed or conditioned, including signal amplification, digitization, or filtering, among others.

In addition to the physiologic signals, other patient information can also be received at 501. For example, patient health information such as past and present medication and therapy information or medical history information, non-clinical information such as patient demographic information, or social and behavioral information (e.g., smokers or non-smokers) can be received at 501 and used by method 500 in predicting likelihood of a target physiologic event.

At 502, two or more signal trends can be generated. The signal trends can be a time series of a statistical or morphological feature derived from the physiologic signal. Examples of signal features can include: signal mean, median, or other central tendency measures; a histogram of the signal intensity; a plurality of signal trends over time; one or more signal morphological descriptors; or signal power spectral density at a specified frequency range. The signal features can include components corresponding to physiologic activities. For example, the electrocardiogram or electrogram features can include P wave, R wave, T wave, QRS complex, or other components representing depolarization, hyperpolarization, repolarization, or other electrophysiological properties of the myocardium. The heart sound features can include timing, amplitude, or morphologic characteristics of one or more of S1, S2, S3, or S4 heart sounds. The thoracic impedance features can include maximum, minimum, mean, variance, rate of change, or other statistical or morphological features. The respiration signal features can include respiration rate, respiration depth, tidal volume, minute ventilation, rapid shallow breathing index (RR/TV), or other descriptors.

At 503, at least a first and a second category-specific inputs can be selected. The first category-specific input can include a first portion selected from the plurality of signal trends or from other patient information based on first associative physiologic condition. Likewise, the second category-specific input can include a second portion selected from the plurality of signal trends or from other patient information based on a different second associative physiologic condition. The first and second associative physiologic conditions can be indicative or correlative of a target physiologic event, such as worsening HF.

Various associative physiologic conditions have been identified, including patient clinical signs and manifestations, etiology, comorbidities, therapy history, among others. As previously discussed with reference to FIG. 4, different physiologic signals or signal trends can be selected for a specified associative physiologic condition. Domain knowledge about the correlations between a physiologic signal and an associative physiologic condition can be used for selecting the physiologic signals or signal trends. For example, one or more thoracic impedance signals and the statistical or morphological signal trends derived thereof can be selected for detecting pulmonary edema. One or more of S3 heart sound signals, ventricular pressure signals, pulmonary arterial pressures, or the statistical or morphological signal features derived thereof can be selected for detecting an elevated ventricular filling pressure. One or more of electrocardiograph (ECG), the intracardiac electrogram, heart sounds, chest acceleration signal, or the statistical or morphological features derived thereof (e.g., ST segments or the T-wave alternans) can be selected for detecting an etiologic factor of ischemic cardiomyopathy. Signal trends of levels of creatinine or body urea nitrogen (BUN), BUN/creatinine ratio, or glomerular filtration rate (GFR) can be selected for detecting an associative physiologic condition of renal insufficiency.

Additionally or alternatively, the selection of the category-specific input can be based on types or modalities of the physiologic sensors used for measuring the physiologic signals, patient population-based performance statistics of a physiologic signal or a signal trend derived thereof in detecting an associative physiologic condition, or a patient-specific historical performance of a physiologic signals or a signal trend derived thereof in detecting an associative physiologic condition.

In some examples, the selection of category-specific input for detecting a specified associative physiologic condition can be non-static. For example, the selection of category-specific input can be adapted to changes in a patient or environmental context, or adapted to the changes in performance of a physiologic signal, a signal trend, or a piece of patient health or non-clinical information in a category-specific input. Examples of the adaptive selection of the category-specific inputs are described below, such as with reference to FIG. 6.

At 504, signal trend metrics, such as signal change indicators, can be computed for each of the first portion and the second portion of the signal trends. The signal change indicators can be a qualitative or quantitative description of how much the signal strength changes over time. The signal change indicator can be one of pre-determined levels (e.g., High, Medium, and Low) indicating relative change in signal strength over time. For a signal trend such as a time series of a physiologic parameter, the signal strength between a first segment taken from a first time period and a second segment taken from a non-identical second time period can be calculated. Difference of the signal strength, such as signal amplitude or the like, between the two segments is computed and compared to a plurality of thresholds or a plurality of value range to classify the signal change into one of the pre-determined levels. Other signal trend metrics, such as a signal strength indicator indicating an amplitude or power of the signal trend, or a signal variability indicator indicating a degree of variation over a specified period of time, can be used as an alternative or in addition to the signal change indicators at 504.

At 505, a first categorical risk index can be computed using the first categorical risk indicator, and a second categorical risk index can be computed using the second categorical risk indicator. The categorical risk index can indicate likelihood of the patient developing or presenting an associative physiologic event indicative or correlative of a target physiologic event, such as a HF decompensation event or worsening HF. In some examples, patient information other than the first and second signal indicators, such as patient health information or non-clinical information received at 501, can also be used in calculation of the respective categorical risk indices.

The categorical risk index can be computed using an intra-category sensor fusion of the respective signal indicators or other patient information. The intra-category fusion can be accomplished by using one or a combination of a rule-based model, a decision tree model, a regression model, a neural network model, a random forest, a voting model, a fuzzy logic model, a support vector machine model or any mathematical model that operates on time-series data. The categorical risk index can be a probability value indicating a likelihood of the patient developing a future associative physiologic condition indicative or correlative of worsening HF, such as a pulmonary or a cardiac event, a central or a peripheral congestion event, or other events. In other examples, the categorical risk index can be one of pre-determined class labels indicating presence or absence of an associative physiologic condition (e.g., "Yes" or "No" labels), or a label or a number indicating a tiered severity of the associative physiologic condition (e.g., High, Medium, or Low, or scores 1, 2, and 3 or levels within a range between 1 to 10).

At 506, a composite risk indicator (CRI) can be generated using at least the first and second categorical risk indices. The CRI is indicative of likelihood of a patient developing a target physiologic event such worsening HF. The CRI can be generated using inter-category fusion of some or all of the categorical risk indices. In an example, the CRI can be in a form of a classification decision taken from two or more classes indicating various levels of likelihood of having an impending event of worsening HF. For example, if the categorical risk indices are class labels (e.g., High, Medium, or Low) or a label or a number indicating a tiered severity of the associative physiologic condition (e.g., High, Medium, or Low, or scores 1, 2, and 3 or levels within a range between 1 to 10), the CRI can be determined using decision fusion of the class labels. Examples of the decision fusion method can include majority voting, X-out-of-Y voting, or weighted voting, among others.

The CRI can be a numerical quantity indicating the likelihood of an impending target physiologic event such as worsening HF. For example, if the categorical risk indices are probability values indicating the confidence level of patient developing various types of associative physiologic conditions, the CRI can be computed using a probability fusion of the probability values. Examples of the probability fusion method can include linear or a non-linear combination such as average or weighted summation, or parametric or non-parametric methods such as a decision tree, a neural networks, a Bayesian network, among other machine learning methods.

The inter-category fusion used in CRI computation can be modified by the system end-user or automatically adjusted. The update can be adapted to changing patient context including patient health condition, activities or behaviors, development of new comorbidities, progression of the target physiologic event, or other patient clinical or non-clinical information. In an example where the CRI is computed as a weighted combination of the categorical risk indices, in patients with renal disease, the CRI calculator 231 can reduce the weight assigned to the categorical risk index computed using thoracic impedance, because with the presence of renal dysfunction, change in thoracic impedance or signal trend derived thereof can be less specific to events of worsening HF. The categorical risk index thus computed may have a degraded performance (e.g., higher false positive rate) in predicting a future event of worsening HF. In another example, in patients with chronic obstructive pulmonary disease (COPD), the weights assigned to the categorical risk index computed using respiration rate or other respiration signals or signal trend can be increased, because with the presence of COPD, change in respiration rate can be more sensitive or specific to events of worsening HF.

The modification of the inter-category fusion can also be made in response to a change in performance, reliability, or robustness of a category-specific input (such as a physiologic signal or a signal trend) to the categorical risk analyzer circuits. For example, the categorical risk index that is substantially higher or lower than other categorical risk indices is suspected to be less reliable or potentially affected by interferences or confounding factors, and therefore can be discounted with a reduced weight. In other examples, the inter-category fusion can be modified in response to changing environmental context such as implantable lead revisions, compromise in sensor integrity and quality, or ambient environmental changes. The modification can also be made in response to a change in significance of an associative physiologic condition according to updated domain knowledge such as established evidence of high correlation between an associative physiologic condition and the target physiologic event.

The method 500 can optionally include an operation of generating a report to inform, warn, or alert a system end-user an elevated risk of a patient developing a target physiologic event such as a future worsening HF event. The report can include the CRI with corresponding timeframe within which the risk is predicted, and the categorical risk indices used for computing the CRI. The report can also include recommended actions such as confirmative testing, diagnosis, or therapy options. The report can be presented in one or more media formats including, for example, a textual or graphical message, a sound, an image, or a combination thereof.

Figure 6:
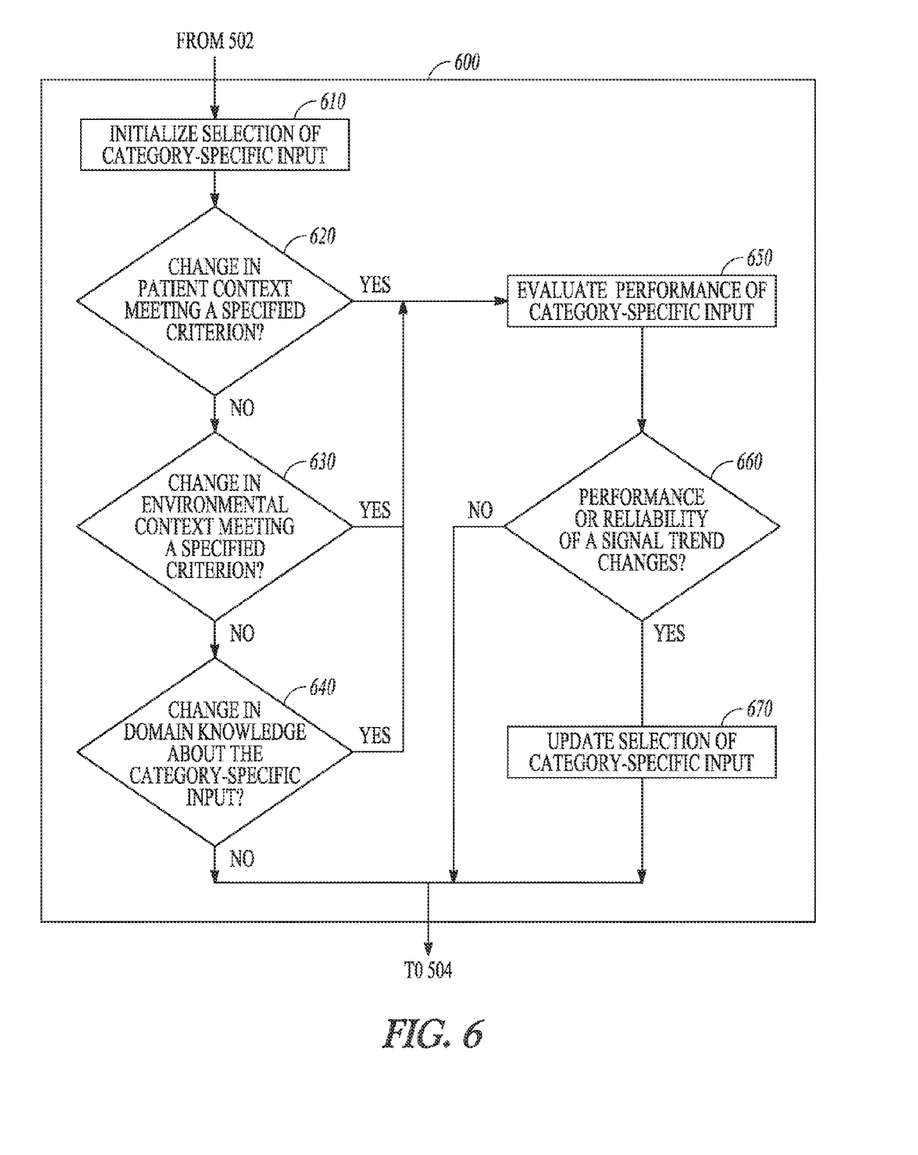
FIG. 6 is a flowchart illustrating an example of a method for adaptively selecting category-specific inputs from a plurality of signal trends or from other patient information.

FIG. 6 is a flowchart illustrating an example of a method 600 for adaptively selecting category-specific inputs from a plurality of signal trends or from other patient information based on a specified associative physiologic condition. The category-specific input for detecting a specified associative physiologic condition can be adapted to changes in one or more conditions. The method 600 can be an embodiment of the process at 503 of FIG. 5 of selecting the first and second portions of signal trends based on their respective associative physiologic condition.

At 610, an initial category-specific input can be selected from the patient information including the signal trends. As previously discussed such as with reference to FIG. 5, the selection can be based on a specified associative physiologic condition. The initial category-specific input can include a plurality of signal trends that are known to be sensitive or specific to the specified associative physiologic condition, such as according to the domain knowledge. A change in patient context can then be evaluated at 620. Changes in patient context can include a change in patient health or medical condition, progression of the target physiologic event such as worsening HF, development of new comorbidities, increase or decrease of activity level, or changes in behaviors, among others.

If the change in patient context is detected and meets a specified criterion at 620, then the performance of the category-specific input is evaluated at 650 to determine if an update to the category-specific input is needed. However, if the change in patient context is not detected, or the change does not meet the specified criterion, then a change in contextual context can be evaluated at 630. The change in environmental context can include non-physiologic events that may affect the accuracy or reliability of the category-specific input in detecting the categorical physiologic condition. For example, following a lead revision, an thoracic impedance signal and signal trends derived thereof can be less sensitive or less reliable in predicting pulmonary edema due to changes electrode positions and tissue-electrode interface properties, both of which may affect the thoracic impedance sensing. Other examples of the change in environmental contexts can include compromise in sensor or lead integrity or lead fracture (e.g., increased lead impedance), increase in environmental noise or interferences causing poor signal-to-noise ratio of the physiologic sensor signals, or ambient environmental changes, among others.

If the change in environmental context is detected and meets a specified criterion at 630, then the performance of the category-specific input is evaluated at 650 to determine if an update to the category-specific input is needed. However, if the change in patient context is not detected, or the change does not meet a specified criterion, then a change in domain knowledge can be evaluated at 640. The domain knowledge can include updates in clinical evidence regarding correlativeness between a physiologic signal or patient information and the associative physiologic condition. If the change in domain knowledge is detected at 640, then the performance of the category-specific input is evaluated at 650 to determine if an update to the category-specific input is needed. Otherwise, the existing category-specific input, including the physiologic signals, signal trends, or patient health and non-clinical information, can remain unchanged and be used for generating signal change indicators, and subsequently for calculating the categorical risk indices, as shown in blocks 504 and 505 in FIG. 5.

The case of an update to the category-specific input is indicated such as due to substantial change in patient context or environmental context, or update in domain knowledge, the exiting category-specific input can be evaluated at 650. The evaluation can include intra-signal evaluation of any change in a performance measure over a period of time. For example, this may involve comparing the performance measure at a present time period against the performance in a historical time period. Examples of the performance measure can include sensitivity, specificity, positive prediction value, negative prediction value, total estimate accuracy or error rate, among others. Additionally or alternatively, the evaluation can include an inter-signal evaluation that involves a comparison of performances among the signal trends and patient information in the category-specific input.

At 660, if the intra-signal evaluation indicates that the performance or signal reliability of a physiologic signal, signal trend, or patient information reduces over time, or if the inter-signal evaluation indicates that one signal trend or sensor signal is substantially outperformed by other signal trends or sensor signals in the category-specific input, then the category-specific input can be updated at 670. Otherwise, the existing category-specific input, including the signal trends or patient health and non-clinical information, can remained unchanged and be used for generating signal change indicators, and subsequently for calculating the categorical risk indices, as shown in blocks 504 and 505 in FIG. 5.

The update of category-specific input at 670 can include removing from the category-specific input the signal trend that either degrades over time in its reliability or performance in detecting the associative physiologic condition, or is consistently outperformed by other signal trends or sensor signals. Likewise, additional physiologic signals, signals trends, or patient information, which are not selected in the initial category-specific input, can be added to the category-specific input if its reliability and performance in detecting the associative physiologic condition improves over time or outperforms a specified number of other signal trends in the category-specific input, or are potentially indicative or correlative of the associative physiologic condition according to updated domain knowledge. In some examples, the update of the category-specific input at 670 can trigger an indication of increasing or decreasing the weights to the signal trend used for calculating the categorical risk index at 505. For example, the weight to a signal trend can be increased if that signal trend consistently outperforms other signal trends in response to a change in patient or environmental context, while the weight to a signal trend can be decreased if that signal trend has degraded performance or reliability over time in response to a change in patient or environmental context. The updated category-specific input can then be used for generating signal change indicators and subsequently for calculating the categorical risk indices, as shown in blocks 504 and 505 in FIG. 5.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including"

and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system, comprising:
   a patient information receiver circuit configured to receive patient information including one or more physiologic signals obtained from a patient, and to generate a plurality of signal trends from the one or more physiologic signals;
   at least two categorical risk analyzer circuits, each including:
      a category-specific input selection circuit configured to receive a category-specific input including at least a portion selected from the plurality of signal trends based on an associative physiologic condition of a different type of condition than and correlative of a target physiologic event;
      a signal trend analyzer circuit configured to generate, for at least one of the selected portion of the plurality of signal trends, a signal trend metric including a signal change indicator indicative of a level of signal change; and
      a categorical risk calculator circuit configured to calculate a categorical risk index using the signal trend metric of the selected portion of the plurality of signal trends, the categorical risk index indicating a likelihood of the patient developing or presenting the associative physiologic condition; and
   a categorical fusion circuit coupled to the at least two categorical risk analyzer circuits, the categorical fusion circuit configured to generate a composite risk indicator using the categorical risk indices respectively provided by the at least two categorical risk analyzer circuits, the composite risk indicator indicative of a likelihood of the patient developing the target physiologic event.

2. The system of claim 1, wherein the category-specific input selection circuit is configured to adaptively update the category-specific input in response to the at least one selected portion of the signal trends meeting a specified criterion.

3. The system of claim 1, wherein the associative physiologic condition includes a specified patient symptom, and the category-specific input selection circuit is configured to receive the category-specific input based on the specified patient symptom.

4. The system of claim 3, wherein the patient symptom includes a symptomatic cardiac event or a symptomatic pulmonary event, and at least one of the at least two categorical risk analyzer circuits is configured to calculate the categorical risk index indicating a likelihood of the patient developing the symptomatic cardiac event or the symptomatic pulmonary event.

5. The system of claim 1, wherein the associative physiologic condition includes a specified etiologic factor of the target physiologic event, and the category-specific input selection circuit is configured to receive the category-specific input based on the specified etiologic factor.

6. The system of claim 5, wherein the etiologic factor includes a patient-specific risk stratifier precipitating the target physiologic event, the categorical risk analyzer is configured to determine the patient-specific risk stratifier, and the category-specific input selection circuit is configured to receive the category-specific input based on the patient-specific risk stratifier.

7. The system of claim 1, wherein the associative physiologic condition includes a specified patient comorbidity condition different from the target physiologic event, and the category-specific input selection circuit is configured to receive the category-specific input based on the patient comorbidity condition.

8. The system of claim 1, wherein the associative physiologic condition includes a specified patient vital sign indicative of one or more of a cardiac exertion, a pulmonary exertion, a blood pressure, or a level of blood oxygenation, and the category-specific input selection circuit is configured to receive the category-specific input based on the patient vital sign.

9. The system of claim 1, wherein the patient information receiver circuit is configured to be capable of receiving patient demographic information, and at least one of the at least two categorical risk calculator circuits is configured to calculate the categorical risk index using the patient demographic information.

10. The system of claim 1, wherein the patient information receiver circuit is configured to be capable of receiving patient therapy information, and at least one of the at least two categorical risk calculator circuits is configured to calculate the categorical risk index using the patient therapy information.

11. The system of claim 1, wherein the signal trend analyzer circuit is configured to generate the signal change indicator including one of a plurality of levels indicating relative change in signal strength over time.

12. The system of claim 1, wherein the categorical risk calculator circuit is configured to calculate a categorical risk index including a linear or a nonlinear combination of the signal change indicators of the at least one selected portion of the plurality of signal trends.

13. The system of claim 1, wherein the categorical risk calculator circuit is configured to calculate a categorical risk index including a categorical decision, and the categorical fusion circuit is configured to generate the composite risk indicator using a decision fusion among the categorical decisions.

14. The system of claim 1, wherein the categorical risk calculator circuit is configured to calculate a categorical risk index including a numerical risk quantity, and the categorical fusion circuit is configured to generate the composite risk indicator using a linear or a non-linear combination of the numerical risk quantities.

15. A method, comprising:
receiving patient information including one or more physiologic signals obtained from a patient;
generating a plurality of signal trends using the one or more physiologic signals;
receiving a first category-specific input including a first portion selected from the plurality of signal trends based on a first associative physiologic condition, and receiving a second category-specific input including a second portion selected from the plurality of signal trends based on a different second associative physiologic condition, the first and second associative physiologic conditions each being of a different type of condition than and correlative of a target physiologic event;
generating first signal trend metrics for the first portion of the signal trends, and generating second signal trend metrics for the second portion of the signal trends, the first and second signal trend metrics including respective first and second signal change indicators each indicative of respective change in signal strength over time;
calculating a first categorical risk index using the first signal trend metrics, and calculating a second categorical risk index using the second signal trend metrics, the first categorical risk index indicating a likelihood of the patient developing or presenting the first associative physiologic condition, the second categorical risk index indicating a likelihood of the patient developing or presenting the second associative physiologic condition; and
generating a composite risk indicator using the first and second categorical risk indices, the composite risk indicator indicative of a likelihood of a patient developing the target physiologic event.

16. The method of claim 15, further comprising adaptively updating the first category-specific input in response to the first selected portion of the signal trends meeting a first specified criterion, or updating the second category-specific input in response to the second selected portion of the signal trends meeting a second specified criterion.

17. The method of claim 15, wherein the first and second associative physiologic conditions each including one or more of a patient symptom, an etiologic factor of the target physiologic event, a patient-specific risk stratifier, a patient comorbidity condition, or a vital signal of the patient.

18. The method of claim 17, wherein the patient symptom includes a symptomatic cardiac event or a symptomatic pulmonary event, wherein calculating the first or second categorical risk index includes calculating the respective risk index indicating a likelihood of the patient developing the symptomatic cardiac event or the symptomatic pulmonary event.

19. The method of claim 15, further comprising receiving at least one of patient demographic information or patient therapy information, wherein calculating the first or second categorical risk index includes calculating the respective risk index using the at least one of the patient demographic information or the patient therapy information.

20. The method of claim 15, wherein the first and second categorical risk indices each includes one of a categorical decision or a numerical risk quantity, and wherein generating the composite risk indicator includes taking a decision fusion of the categorical decisions, or calculating a linear or nonlinear combination of the numerical risk quantities.

* * * * *